(12) United States Patent
Kasumi

(10) Patent No.: US 12,396,620 B2
(45) Date of Patent: Aug. 26, 2025

(54) WIRELESS ENDOSCOPE, WIRELESS ENDOSCOPE APPARATUS AND ILLUMINATION CONTROL METHOD

(71) Applicant: OLYMPUS CORPORATION, Tokyo (JP)

(72) Inventor: Makoto Kasumi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 718 days.

(21) Appl. No.: 17/487,735

(22) Filed: Sep. 28, 2021

(65) Prior Publication Data

US 2022/0021801 A1    Jan. 20, 2022

Related U.S. Application Data

(63) Continuation of application No. PCT/JP2019/014744, filed on Apr. 3, 2019.

(51) Int. Cl.
*A61B 1/00* (2006.01)
*A61B 1/06* (2006.01)
(Continued)

(52) U.S. Cl.
CPC ...... *A61B 1/00016* (2013.01); *A61B 1/00006* (2013.01); *A61B 1/00032* (2013.01); *A61B 1/00039* (2013.01); *A61B 1/0004* (2022.02); *A61B 1/00042* (2022.02); *A61B 1/0655* (2022.02); *G10L 15/22* (2013.01); *G10L 25/78* (2013.01); *H04N 5/38* (2013.01); *H04N 7/18* (2013.01); *H04N 23/56* (2023.01);
(Continued)

(58) Field of Classification Search
None
See application file for complete search history.

(56) References Cited

U.S. PATENT DOCUMENTS

2005/0033144 A1* 2/2005 Wada .............. A61B 7/003
600/407
2015/0031954 A1 1/2015 Kimoto et al.
(Continued)

FOREIGN PATENT DOCUMENTS

CN    104203071 A    12/2014
CN    107105999 A    8/2017
(Continued)

OTHER PUBLICATIONS

International Search Report dated Jul. 2, 2019 received in PCT/JP2019/014744.
Abstract only of WO 2015/110525 A1.

*Primary Examiner* — Samira Monshi
(74) *Attorney, Agent, or Firm* — Scully, Scott, Murphy & Presser, P.C.

(57) ABSTRACT

A wireless endoscope includes: a wireless receiving circuit configured to receive a wirelessly transmitted voice; a first processor configured to process the voice received by the wireless receiving circuit; a light source apparatus configured to generate illumination light to illuminate a subject; an image pickup sensor configured to pick up an image of the subject; a wireless transmission circuit configured to wirelessly transmit an image pickup result of the image pickup sensor; and a second processor configured to control the light source apparatus based on a processing result of the first processor.

19 Claims, 7 Drawing Sheets

(51) Int. Cl.
  *G10L 15/22*   (2006.01)
  *G10L 25/78*   (2013.01)
  *H04N 5/38*    (2006.01)
  *H04N 7/18*    (2006.01)
  *H04N 23/56*   (2023.01)
  *H04N 23/74*   (2023.01)
  *A61B 1/04*    (2006.01)
  *H04N 23/50*   (2023.01)

(52) U.S. Cl.
  CPC .............. *H04N 23/74* (2023.01); *A61B 1/044* (2022.02); *A61B 1/06* (2013.01); *H04N 23/555* (2023.01)

(56) References Cited

U.S. PATENT DOCUMENTS

| | | | |
|---|---|---|---|
| 2017/0079517 A1 | 3/2017 | Özcan et al. | |
| 2017/0281045 A1* | 10/2017 | Kagawa | A61B 1/0661 |
| 2019/0142256 A1* | 5/2019 | Zhao | A61B 1/00029 |
| | | | 600/109 |

FOREIGN PATENT DOCUMENTS

| | | | |
|---|---|---|---|
| CN | 107510432 A | 12/2017 | |
| JP | 2000-300514 A | 10/2000 | |
| JP | 6412145 B2 | 10/2018 | |
| WO | 03/068056 A1 | 8/2003 | |
| WO | 2015/167414 A1 | 11/2015 | |

\* cited by examiner

WIRELESS ENDOSCOPE, WIRELESS ENDOSCOPE APPARATUS AND ILLUMINATION CONTROL METHOD

CROSS REFERENCE TO RELATED APPLICATION

This application is a continuation application of PCT/R2019/014744 filed on Apr. 3, 2019, the entire contents of which are incorporated herein by this reference.

BACKGROUND OF THE INVENTION

1. Field of the Invention

The present invention relates to a wireless endoscope, a wireless endoscope apparatus and an illumination control method that are suitable for vocal cord observation.

2. Description of the Related Art

Conventionally, an endoscope system has been widely used. In the endoscope system, an elongated endoscope is inserted into a body cavity or the like, and observation or various treatments of a site to be examined are performed. An endoscope image obtained by an image pickup device of the endoscope is transmitted to a video processor that performs signal processing. The video processor performs the signal processing of the image from the endoscope, and supplies the image to a monitor for display or supplies the image to a recording apparatus for recording.

A scope cable is used for transmitting the endoscope image from the endoscope to the video processor. However, by the scope cable, the movement range of the endoscope can be restricted or the operability can be impaired. Further, the scope cable can be tangled in another cable, causing a failure such as disconnection. Hence, in recent years, there has been developed a wireless endoscope that is equipped with a rechargeable battery and that wirelessly transmits the endoscope image to the processor and the like.

In some cases, vocal cord observation is performed by the endoscope. For the observation of vocal cord vibration, stroboscopic observation is employed. In the stroboscopic observation, an observation image is obtained using a so-called stroboscopic effect by which the vocal cords look as if the vocal cords were slowly vibrating by blinking stroboscopic light with a period slightly different from the period of the vocal cord vibration.

In the stroboscopic observation with the endoscope, for example, voice analysis is performed based on an acquired sound, and light emission (stroboscopic light emission) is performed at light emission timings decided from the result of the voice analysis (see Japanese Patent Application Laid-Open Publication No. 2000-300514, for example). Accordingly, a microphone for acquiring the voice of a patient is necessary for the stroboscopic observation of the vocal cords.

Note that the wireless endoscope can be employed as an endoscope that allows the observation of vocal cords in the stroboscopic observation.

SUMMARY OF THE INVENTION

A wireless endoscope according to an aspect of the present invention includes: a wireless receiving circuit configured to receive a wirelessly transmitted voice; a first processor configured to process the voice received by the wireless receiving circuit; a light source apparatus configured to generate illumination light to illuminate a subject; an image pickup sensor configured to pick up an image of the subject; a wireless transmission circuit configured to wirelessly transmit an image pickup result of the image pickup sensor; and a second processor configured to control the light source apparatus based on a processing result of the first processor.

A wireless endoscope apparatus according to an aspect of the present invention includes a wireless endoscope and a voice detection unit, the voice detection unit including: a microphone configured to detect a voice; a voice modulation circuit configured to modulate the voice detected by the microphone; and a first wireless transmission circuit configured to wirelessly transmit a modulation result of the voice modulation circuit, the wireless endoscope including: a wireless receiving circuit configured to receive the voice wirelessly sent from the first wireless transmission circuit; a first processor configured to process the voice received by the wireless receiving circuit; a light source apparatus configured to generate illumination light to illuminate a subject; an image pickup sensor configured to pick up an image of the subject; a second wireless transmission circuit configured to wirelessly transmit an image pickup result of the image pickup sensor; and a second processor configured to control the light source apparatus based on a processing result of the first processor.

An illumination control method according to an aspect of the present invention is an illumination control method for controlling illumination light of a wireless endoscope, in which: a voice detection unit detects a voice, modulates the detected voice, and wirelessly transmits a signal for the modulated voice; and a wireless endoscope receives the wirelessly transmitted voice, and controls light emission by giving a processing result of the wirelessly received voice, to a light source apparatus configured to generate illumination light to illuminate a subject.

DETAILED DESCRIPTION OF THE PREFERRED EMBODIMENTS

Embodiments of the present invention will be explained below in detail, with reference to the drawings.

First Embodiment

Figure 1:
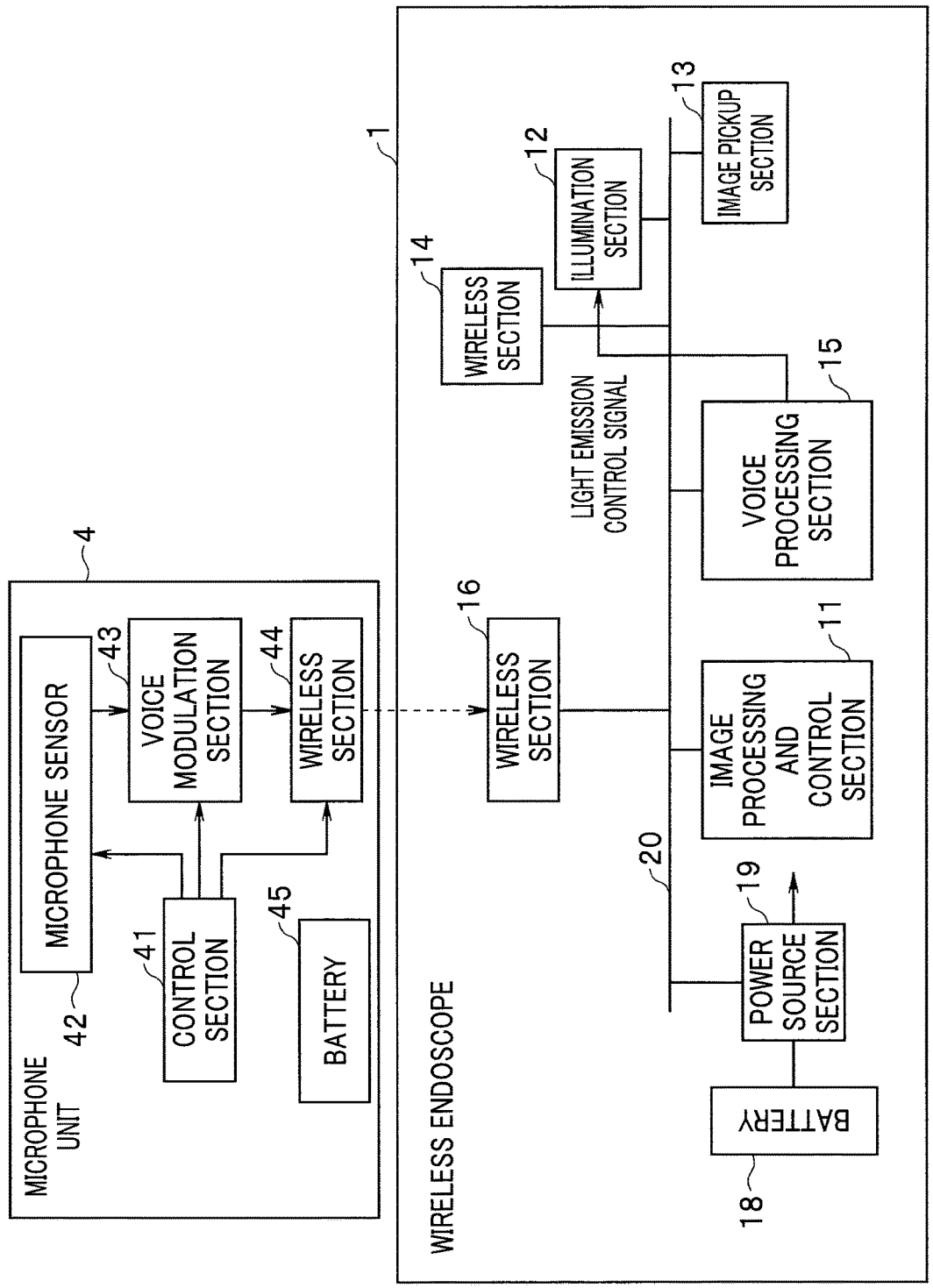
FIG. 1 is a block diagram showing a circuit configuration of a principal part of a wireless endoscope apparatus according to a first embodiment of the present invention.
Figure 2:
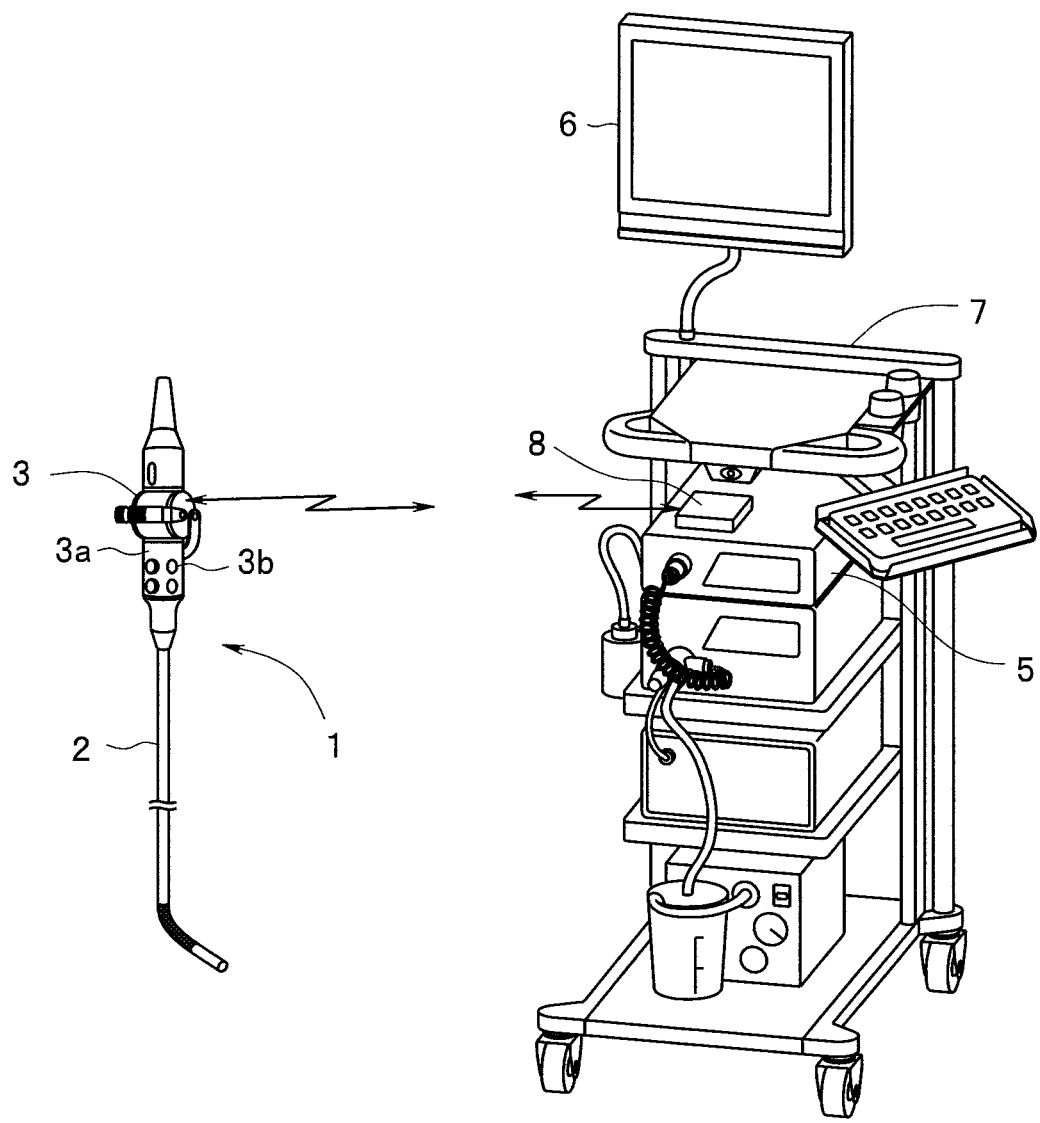
FIG. 2 is an explanatory diagram showing an outline of a whole configuration of an endoscope system including the wireless endoscope apparatus.
Figure 3:
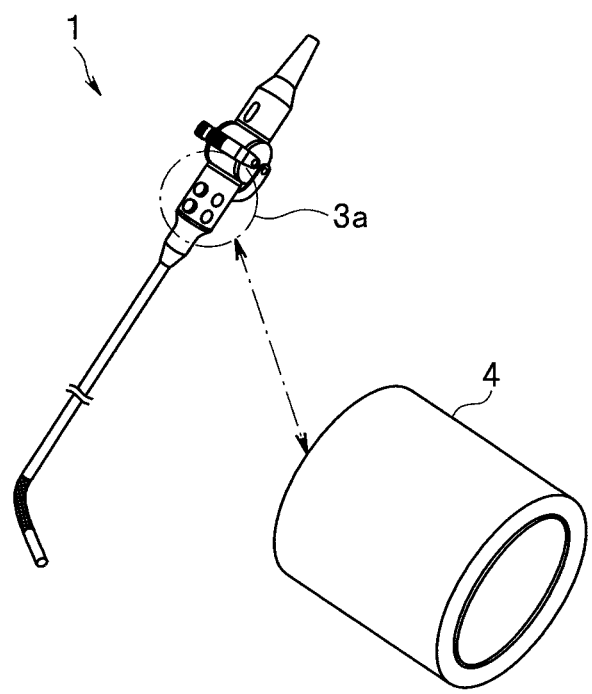
FIG. 3 is an explanatory diagram for explaining an attachment position of a microphone unit on a wireless endoscope.

FIG. 1 is a block diagram showing a circuit configuration of a principal part of a wireless endoscope apparatus according to a first embodiment of the present invention. FIG. 2 is an explanatory diagram showing an outline of a whole configuration of an endoscope system including the wireless endoscope apparatus. FIG. 3 is an explanatory diagram for explaining an attachment position of a microphone unit on a wireless endoscope. In the embodiment, the microphone unit and the wireless endoscope are wirelessly connected, and stroboscopic light emission is controlled by detection of attachment of the microphone unit, so that stroboscopic observation using the wireless endoscope can be performed.

First, an outline of the endoscope system employing a wireless endoscope will be explained with reference to FIG. 2 and FIG. 3. The endoscope system in FIG. 2 includes the wireless endoscope 1, a video processor 5 and a monitor 6. Various medical instruments and the monitor 6 are disposed on a cart 7. Further, the video processor 5 connected with a wireless section 8 is placed on the cart 7. Note that apparatuses such as an electric cautery apparatus, an insufflation apparatus and a video recorder, and a gas cylinder filled with carbon dioxide also are placed on the cart 7 as medical instruments, for example.

The wireless endoscope 1 can perform a photographing operation for ordinary endoscope observation when an unillustrated battery is mounted, and has a wireless configuration of being wirelessly connected with the video processor 5.

The wireless endoscope 1 is configured by an endoscope body including an insertion section 2 on a distal end side and including an operation section 3 on a proximal end side. An unillustrated image pickup section as an image pickup sensor is arranged at a distal end portion of the insertion section 2. The image pickup section includes an image pickup device configured by a CCD, a CMOS sensor or the like. Further, an unillustrated illumination section configured to generate illumination light for illuminating a photographic subject is provided in the insertion section 2, The illumination section as an in-scope light source irradiates the photographic subject with the generated light as the illumination light, through an unillustrated lens al a distal end of the insertion section 2.

Return light from the photographic subject enters an unillustrated observation lens at the distal end of the insertion section 2, and forms an image on an image pickup surface of the image pickup section. The image pickup section obtains a. pickup image based on a photographic subject optical image, by photoelectric conversion. The image pickup section transmits the pickup image to an unillustrated substrate in the operation section 3, through an unillustrated signal wire in the insertion section 2. The unillustrated substrate provided in the operation section 3 is equipped with various circuits including an unillustrated image processing circuit and a communication circuit configured to perform signal transmission, and by the circuits, the pickup image is wirelessly transmitted to the wireless section 8. Note that a plurality of endoscope switches 3b are arranged on an operation surface 3a of the operation section 3 and operation signals based on operations of the endoscope switches 3b are also transmitted to the wireless section 8.

The communication circuit incorporated in the wireless endoscope 1 can transmit and receive not only the pickup image but also drive signals and a variety of setting information, for the wireless section 8. By the drive signals, the image pickup device and the illumination section arranged in the insertion section 2 are driven.

Note that although the image pickup section and the illumination section have been explained as an image pickup section and an illumination section that are provided at the distal end of the insertion section 2, the image pickup section may be provided on the side of the operation section 3 as in a case of a camera head, a light source may be provided in the operation section 3 or the like and the illumination light may be guided to the distal end of the insertion section 2 by a light guide or the like.

Note that a battery 18 is incorporated in the wireless endoscope 1 and electric power from the battery 18 is supplied to a power source section 19 equipped on the substrate in the operation section 3.

As shown in FIG. 3, an unillustrated locking portion for attaching a microphone unit 4 is provided on the operation surface 3a. of the operation section 3. The microphone unit 4 as a voice detection unit can be removably attached on the operation surface 3a. At the time of stroboscopic observation, the microphone unit 4 is attached to the locking portion. The microphone unit 4 acquires a voice in a periphery, and transmits the acquired voice to the wireless endoscope 1.

Next, specific configuration examples of the wireless endoscope 1 and the microphone unit 4 will be explained with reference to FIG. 1.

In the microphone unit 4, a control section 41, a microphone sensor 42, a voice modulation section 43, a wireless section 44 and a battery 45 are provided. The control section 41 may be configured by a processor using a CPU, an FPGA or the like, and may control each section by operating in accordance with a program stored in an unillustrated memory. Some or all functions may be realized by an electronic circuit of hardware.

As the microphone sensor 42, various microphones such as a capacitor type and a dynamic type can be employed. The microphone sensor 42 as a voice detection section acquires the voice in the periphery, and outputs the acquired voice to the voice modulation section 43. As the voice modulation section 43, for example, modulation circuits employing digital modulation schemes such as QAM (quadrature amplitude modulation) and various other modulation schemes can be used. The voice modulation section 43 as a voice modulation circuit modulates the voice given from the microphone sensor 42, and outputs the voice to the wireless section 44. The wireless section 44 as a first wireless transmission circuit is configured by a communication circuit configured to operate under a predetermined wireless scheme. For example, the wireless section 44 may be capable of performing a short-range wireless communication, and may employ a wireless standard such as Wi-Fi (registered trademark) and Bluetooth (registered trademark). The wireless section 44 wirelessly transmits the voice from the voice modulation section 43.

The voice wirelessly transmitted from the wireless section 44 can be received by a wireless section 16 of the wireless endoscope 1. The wireless section 16 as a wireless receiving circuit is a communication circuit that operates under a wireless standard corresponding to the wireless section 44. The wireless section 16 receives the voice transmitted from the wireless section 44, and outputs the received voice to an image processing and control section 11 through a bus 20.

The image processing and control section 11 (also referred to as a control section 11, hereinafter) of the wireless endoscope 1 may be configured by a processor using a CPU, an FPGA or the like, and may control each section by operating in accordance with a program stored in an unillustrated memory. Some or all functions may be realized by an electronic circuit of hardware. The control section 11 as a second processor is connected with the bus 20, and controls each section through the bus 20.

In the wireless endoscope 1, an illumination section 12 is provided. The illumination section 12 as a light source apparatus is configured by various light source apparatus such as an LED (light-emitting diode) light source. The illumination section 12 generates the illumination light by being controlled by the image processing and control section 11. The photographic subject is irradiated with the illumination light from the illumination section 12, through an unillustrated illumination lens provided at a distal end portion of the insertion section 2.

The illumination section 12 performs switching between ordinary light emission and stroboscopic light emission by being controlled by the control section 11. Further, a light emission control signal is given to the illumination section 12 by a voice processing section 15 described later, and the light emission period at the time of the stroboscopic light emission is controlled based on the light emission control signal.

In the wireless endoscope 1, an image pickup section 13 is provided at a distal end portion of the insertion section 2. The image pickup section 13 includes an unillustrated image pickup device such as a CCD or a CMOS sensor, and reflected light from the photographic subject enters an image pickup surface through an unillustrated observation lens. The image pickup section 13 obtains a pickup image by photoelectric conversion of a photographic subject optical image that enters the image pickup surface. The image processing and control section 11 drives the image pickup section 13, and receives the pickup image from the image pickup section 13, to output the pickup image to a wireless section 14 after performing a predetermined image signal process.

The wireless section 14 as a second wireless transmission circuit is configured by a communication circuit that employs a predetermined wireless standard such as Wi-Fi. The wireless section 14 modulates the pickup image from the image processing and control section 11, and thereafter wirelessly transmits the pickup image. The signal transmitted from the wireless section 14 is received by the wireless section 8, and is supplied to the video processor 5. Further, the wireless section 14 receives various control signals and the like transmitted from the video processor 5 through the wireless section 8, and gives the control signals and the like to the image processing and control section 11.

The battery 18 is provided in the wireless endoscope 1. The battery 18 generates a predetermined electric power, and supplies the electric power to the power source section 19. The power source section 19 can be configured by a power source circuit configured to generate power source voltage to he used in each section of the wireless endoscope 1 by the electric power from the battery 18. The power source section 19 supplies the generated power source voltage to each section of the wireless endoscope 1, by being controlled by the image processing and control section 11 (not illustrated).

In the embodiment, the image processing and control section 11 performs the stroboscopic light emission of the illumination section 12, only in a case where the microphone unit 4 is removably attached on the operation surface 3a or in a case where a voice having a level equal to or higher than a predetermined level is supplied from the microphone unit 4.

For example, when the wireless communication between the wireless section 16 and the wireless section 44 is established, the image processing and control section 11 may determine that the microphone unit 4 has been attached to the operation surface 3a, and may control the illumination section 12 such that the stroboscopic light emission is started. Further, in a case where the receiving level of the voice received by the wireless section 16 exceeds a predetermined threshold when the receiving level of the voice and the threshold are compared, the image processing and control section 11 may determine that a sufficient level of voice has been outputted from the microphone unit 4. and may control the illumination section 12 such that the stroboscopic light emission is started.

The voice received by the wireless section 16 is supplied to the voice processing section 15 as a first processor. The voice processing section 15 as the voice processing section may be configured by a processor using a CPU, an FPGA or the like, and may control each section by operating in accordance with a program stored in an unillustrated memory. Some or all functions may be realized by an electronic circuit of hardware. The voice processing section 15 evaluates the voice frequency of the inputted voice by voice analysis, generates the light emission control signal based on the evaluated voice frequency, and outputs the light emission control signal to the illumination section 12. The illumination section 12 performs the stroboscopic light emission with a period based on the light emission control signal.

The voice processing section 15 is a circuit section necessary for the stroboscopic observation. Hence, in the embodiment, to reduce electric power consumption, the image processing and control section 11 may set a time period during which the wireless communication with the wireless section 44 in the wireless section 16 is established or a time period during which the voice receiving level in the wireless section exceeds the threshold, as a stroboscopic observation time period, and may control the power source section 19 such that the power source voltage is supplied to the voice processing section 15 only during the time period.

Figure 4:
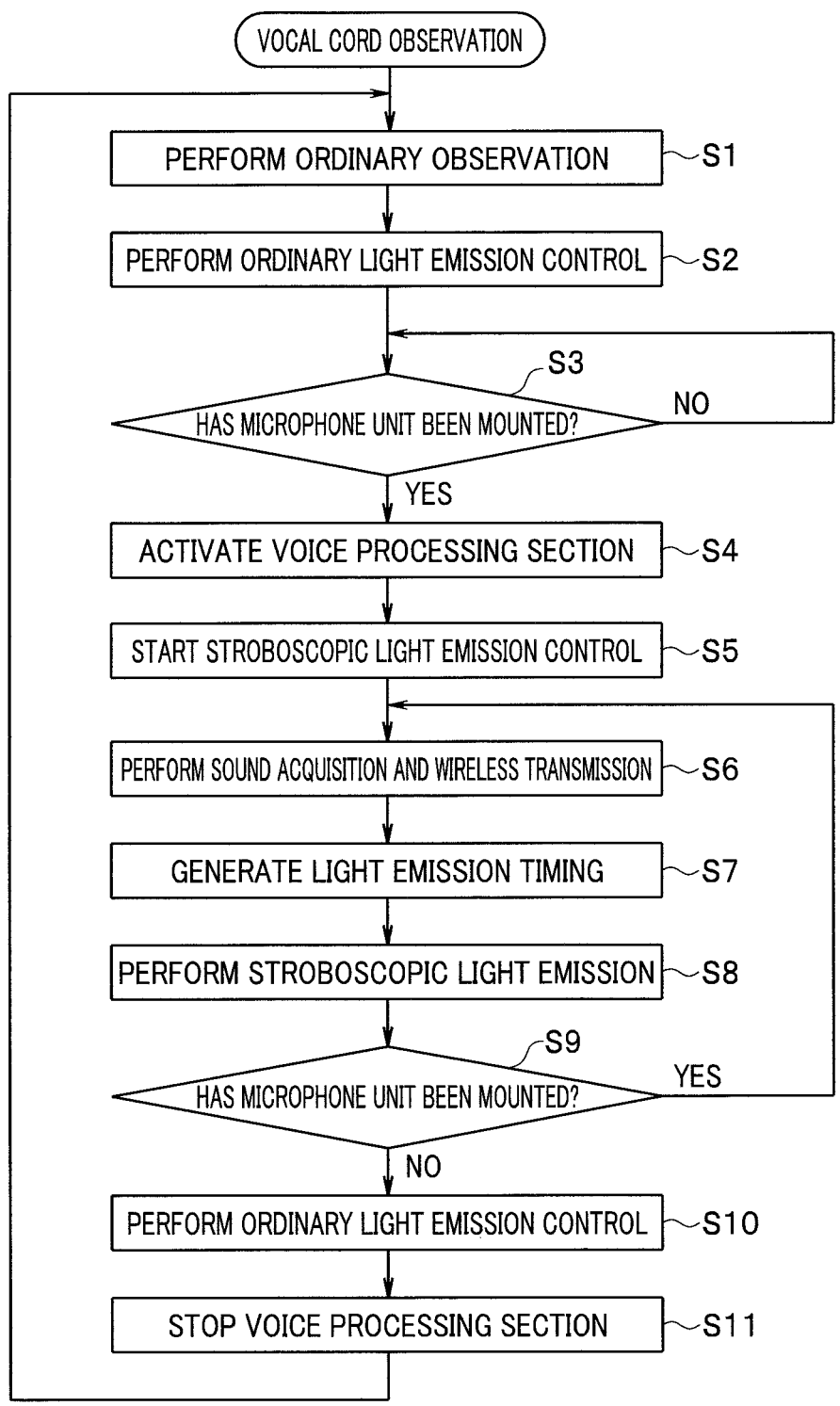
FIG. 4 is a flowchart for explaining an operation of the first embodiment.
Figure 5:
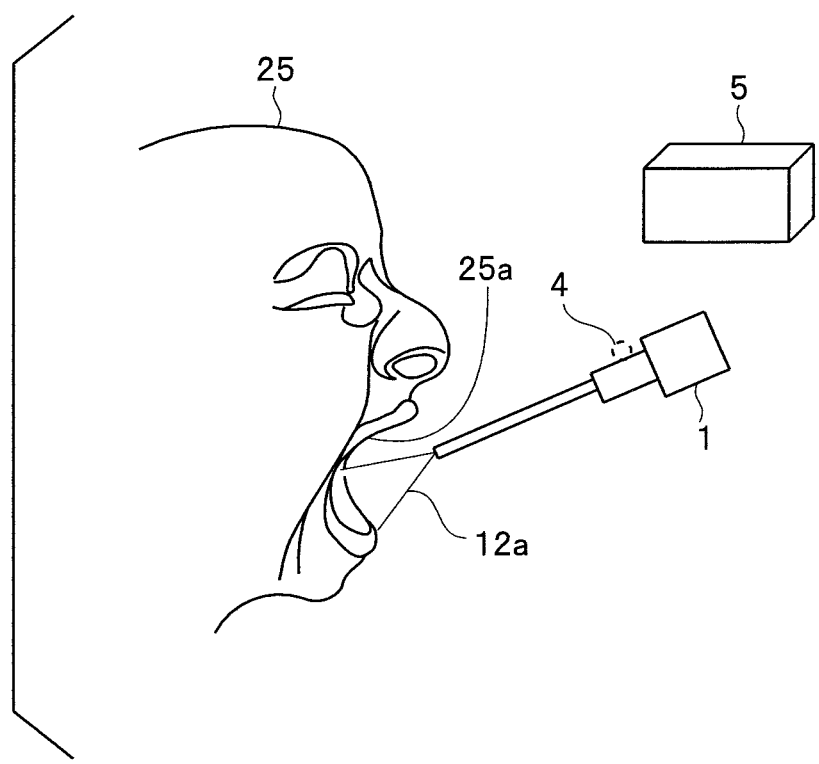
FIG. 5 is an explanatory diagram for explaining a manner of stroboscopic observation in the embodiment.

Next, an operation of the embodiment configured in this way will be explained with reference to FIG. 4 and FIG. 5. FIG. 4 is a flowchart for explaining the operation of the embodiment. FIG. 5 is an explanatory diagram for explaining a manner of the stroboscopic observation in the embodiment.

As shown in FIG. 5, in the vocal cord observation, first, the insertion section 2 of the wireless endoscope 1 is inserted into a mouth 25a of a subject 25, such that the distal end of the insertion section 2 reaches a position allowing the vocal cord observation. During the insertion, an ordinary light observation with ordinary light is performed such that a state at the time of the insertion can he observed (step S1 in FIG. 4). In other words, the image processing and control section 11 controls the illumination section 12, such that the ordinary light is emitted (step S2).

The image pickup section 13 performs the photoelectric conversion of the return light from the subject 25 illuminated by the illumination section 12, arid outputs the pickup image to the image processing and control section 11. The image processing and control section 11 performs the predetermined image signal process to the pickup image, and thereafter transmits the pickup image to the video processor 5 through the wireless section 14. The video processor 5 generates an image based on the pickup image, and outputs the image to the monitor 6. Thus, the pickup image at the time of the insertion is displayed on a display screen of the monitor 6.

When an operator inserts the insertion section 2 to the position allowing the vocal cord observation, the operator mounts the microphone unit 4 on the operation surface 3a. Note that a position where the microphone unit 4 is mounted is shown by a broken line in FIG. 5. In step S3, the image processing and control section 11 determines whether the microphone unit 4 has been mounted. When the microphone unit 4 has been mounted, the wireless communication between the wireless section 44 and the wireless section 16 is established. Information indicating the establishment of the wireless communication is given to the image processing and control section 11. Thereby, the image processing and control section 11 determines that the microphone unit 4 has mounted on the operation surface 3a, and transfers the process from step S3 to step S4. Steps S4 to S8 show processes in the stroboscopic observation time period. The image processing and control section H starts the supply of the power source voltage from the power source section 19 to the voice processing section 15, and activates the voice processing section 15 (step S4). The control section 11 causes the illumination section 12 to start the stroboscopic light emission (step S5).

The microphone unit 4 acquires the voice of the subject through the microphone sensor 42 (step S6). The voice from the microphone sensor 42 is modulated by the voice modulation section 43, and is supplied to the wireless section 44. The wireless section 44 wirelessly transmits the voice. The wireless section 16 of the wireless endoscope 1 receives the voice transmitted from the wireless section 44, and supplies the voice to the voice processing section 15 through the bus 20. The voice processing section 15 evaluates the voice frequency from the inputted voice. The voice processing section 15 generates the light emission control signal for causing the illumination section 12 to perform the stroboscopic light emission at a frequency close to the voice frequency, based on the evaluated voice frequency, and supplies the light emission control signal to the illumination section 12 (step S7). The illumination section 12 performs the stroboscopic light emission at the light emission frequency based on the light emission control signal (step S8).

Thus, the vocal cords are illuminated by the stroboscopic light emission. The image pickup section 13 performs the photoelectric conversion of the return light from the vocal cords illuminated by the stroboscopic light emission, and outputs the pickup image to the image processing and control section 11. The image processing and control section 11 performs the predetermined image signal process to the pickup image, and thereafter transmits the pickup image to the video processor 5 through the wireless section 14. The video processor 5 generates an image based on the pickup image, and outputs the pickup image to the monitor 6. Thus, an image in which the vocal cords slowly vibrate is displayed on a display screen of the monitor 6, so that the stroboscopic observation can be performed. The processes in steps S6 to S8 are repeated until it is detected that the microphone unit 4 has been detached in step S9.

The operator detaches the microphone unit 4 for ending the stroboscopic observation. In step S9, the image processing and control section 11 determines whether the microphone unit 4 has been mounted. The wireless communication between the wireless section 44 of the microphone unit 4 and the wireless section 16 is cancelled by the increase in the distance between the two. From the output of the wireless section 16, the image processing and control section 11 detects that the wireless communication has been cancelled, namely, that the microphone unit 4 has been detached. Then, the image processing and control section 11 controls the illumination section 12 to perform the ordinary light emission control, and ends the stroboscopic observation time period (step S10). In step S11, the image processing and control section 11 stops the power supply to the voice processing section 15, and stops the operation of the voice processing section 15. Thus, the return to the ordinary light observation is performed.

Note that the switching between the stroboscopic observation time period and the ordinary light observation time period may be performed in a state where the microphone unit 4 is mounted, although the switching between the stroboscopic observation time period and the ordinary light observation time period is performed by the determination of the establishment or cancellation of the wireless communication from the attachment or detachment of the microphone unit 4. For example, the control section 11 may start the stroboscopic light emission when the level of the voice supplied from the microphone unit 4 to the wireless endoscope exceeds a predetermined threshold, and may recover the ordinary light observation when the level of the voice becomes lower than the predetermined threshold.

Second Embodiment

Figure 6:
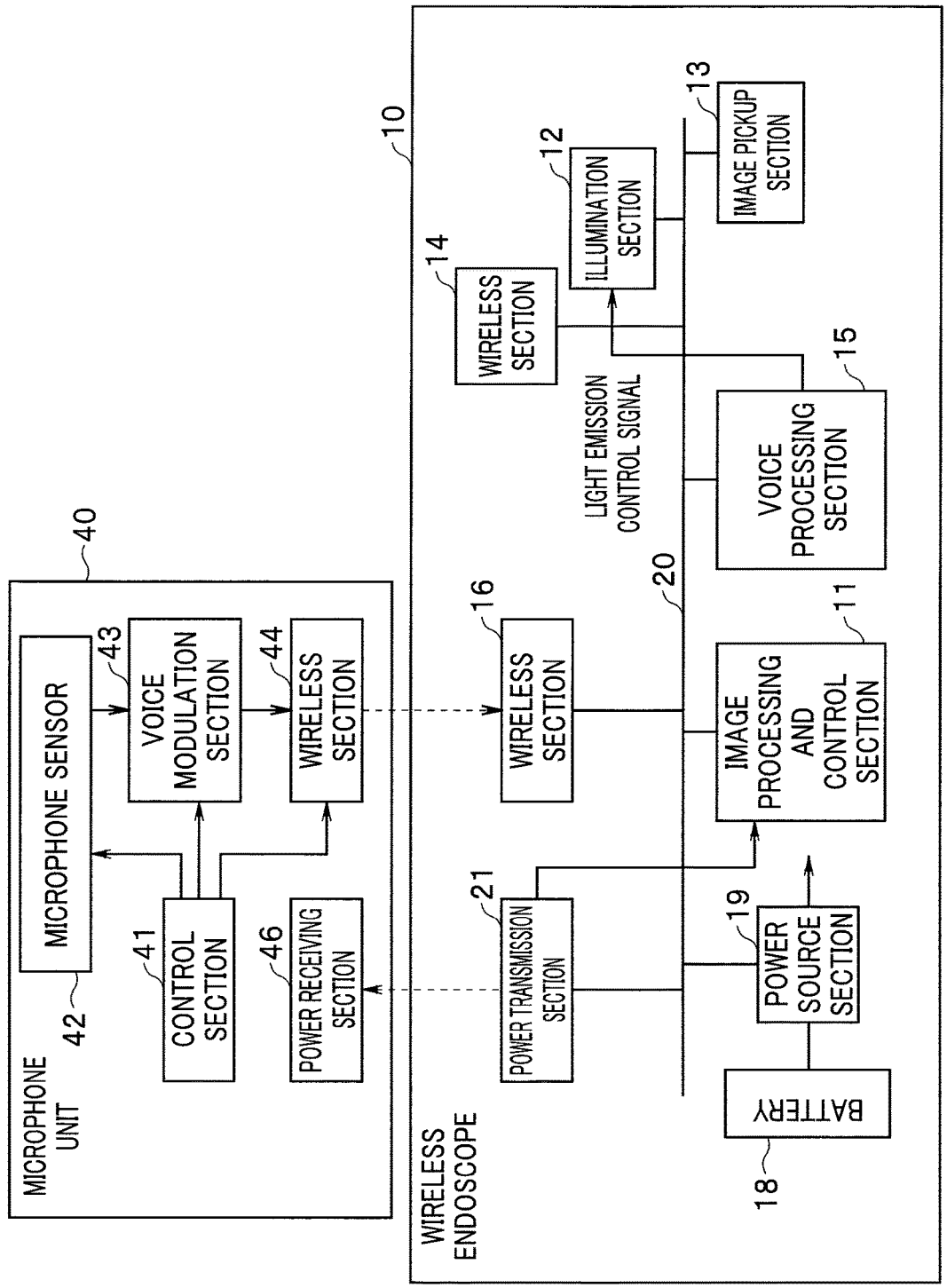
FIG. 6 is a block diagram showing a second embodiment of the present invention.

FIG. 6 is a block diagram showing a second embodiment of the present invention. In FIG. 6, the same component elements as component elements in FIG. 1 are denoted by the same reference characters, and the explanation is omitted. The embodiment allows the management of electric power in a case of employing a microphone unit that includes no battery.

A microphone unit 40 is different from the microphone unit 4 in FIG. 1, in that the microphone unit 40 includes a power receiving section 46 as a power receiving circuit instead of the battery 45. Further, a wireless endoscope 10 is different from the wireless endoscope 1 in FIG. 1, in that a power transmission section 21 as a power transmission circuit is added. The power transmission section 21 transmits the electric power from the power source section 19 to the microphone unit 40, by being controlled by the image processing and control section 11. The power receiving section 46 receives the electric power transmitted from the power transmission section 21. For example, the power transmission section 21 and the power receiving section 46 are configured by coils, and are electromagnetically coupled, so that the transmission of the electric power can be performed. The power receiving section 46 can receive the supply of the electric power from the power transmission section 21, by approaching the power transmission section 21. The power receiving section 46 generates power source voltage to be used in each section in the microphone unit 40, by the received electric power.

In the embodiment, the power transmission section 21 can detect whether the power transmission section 21 is supplying electric power to the power receiving section 46. For example, in a case where the power transmission section 21 detects that the power transmission section 21 is supplying electric power to the power receiving section 46, the power transmission section 21 outputs a detection signal to the image processing and control section 11. The image processing and control section 11 sets the stroboscopic observation time period based on the detection signal from the power transmission section 21. Note that the image processing and control section 11 may set the stroboscopic observation time period when the electric consumption amount of the power transmission section 21 exceeds a predetermined reference value. For example, the image processing and control section H may detect that the electric consumption in the microphone unit 40 is increased for transmitting a voice having a level equal to or higher than a predetermined level, and may set the stroboscopic observation time period.

Note that the image processing and control section 11 may set the stroboscopic observation time period by monitoring the electric consumption amount of the power transmission section 21 based on information from the power source section 19.

Figure 7:
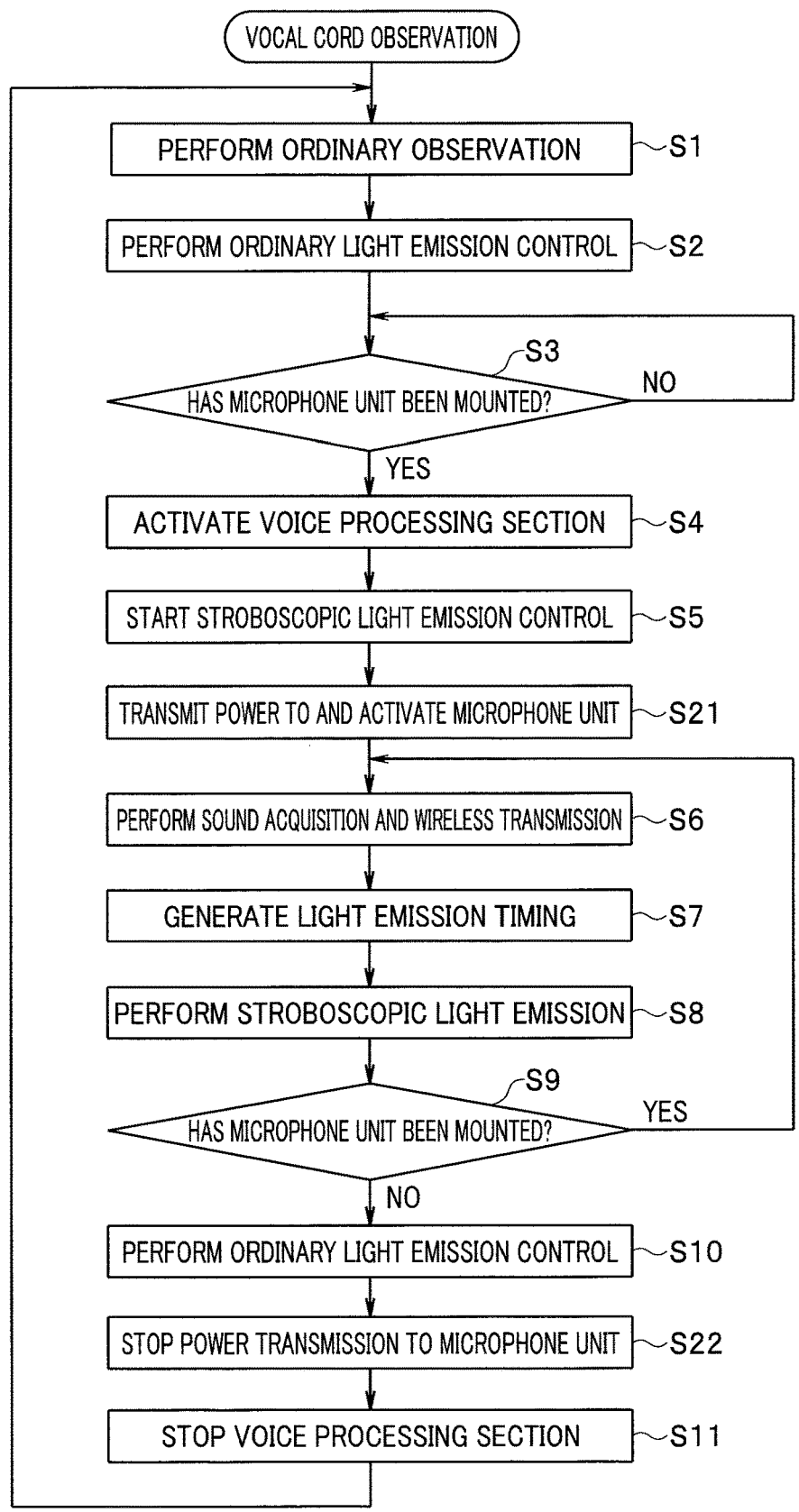
FIG. 7 is a flowchart for explaining an operation of the second embodiment.

Next, an operation of the embodiment configured in this way will be explained with reference to FIG. 7. FIG. 7 is a flowchart for explaining the operation of the embodiment. In FIG. 7, the same procedures as procedures in FIG. 4 are denoted by the same reference characters, and the explanation is omitted.

In the embodiment, in step S3 of FIG. 7, the mounting of the microphone unit 40 is detected based on determination of whether the power transmission section 21 and the power receiving section 46 have been electromagnetically coupled. When the image processing and control section 11 detects the electromagnetic coupling between the power transmission section 21 and the power receiving section 46, the image processing and control section 11 determines that the microphone unit 40 has been mounted on the operation surface 3a, and transfers the process from step S3 to step S4.

The image processing and control section 11 starts the supply of the power source voltage from the power source section 19 to the voice processing section 15, and activates the voice processing section 15. In step S5, the image processing and control section 11 starts the stroboscopic light emission. Furthermore, the image processing and control section 11 causes the power transmission section 21 to start the power transmission to the microphone unit 40, and activates the microphone unit 40 (step S21). The microphone unit 40 becomes capable of operating when the power receiving section 46 receives the supply of electric power, and the microphone sensor 42 acquires the voice of the subject by being controlled by the control section 41 (step S6). Thus, in the embodiment, the stroboscopic observation can be performed.

In the embodiment, in step S9 of FIG. 7, it is detected that the microphone unit 40 has been detached, based on a determination that the power transmission section 21 and the power receiving section 46 are electromagnetically decoupled. When the image processing and control section 11 detects that the microphone unit 40 has been detached, the image processing and control section 11 performs an ordinary light emission control in step S10, and thereafter stops the power transmission to the microphone unit 40 in step S22. Note that the power transmission is sometimes stopped automatically when the power receiving section 46 gets away from the power transmission section 21. In step S11, the image processing and control section 11 stops the power supply to the voice processing section 15, and stops the operation of the voice processing section 15.

In this way, in the embodiment, it is possible to obtain the same effect as the effect in the first embodiment. Further, in the embodiment, in the case where electric power is supplied from an endoscope processor to the microphone unit, the electric power is supplied to the microphone unit only when the microphone unit is used, so that the increase in electric consumption can be restrained.

In the above embodiment, the example in which the stroboscopic observation time period is set by monitoring the supply of electric power from the power transmission section to the microphone unit, but the stroboscopic observation time period may be set by receiving a voice having a level higher than a predetermined level after the microphone unit starts to operate by receiving the supply of electric power.

Note that the stroboscopic observation time period, a time period during which the illumination section performs the stroboscopic light emission, a time period during which the voice processing section is activated, and a time period during which electric power is supplied to the microphone unit do not always coincide with each other in the above respective embodiments.

In the technologies explained in the specification, for controls explained mainly with the flowcharts, programs can be often set, and are sometimes stored in a recording medium or a recording section. As methods for the recording in the recording medium or the recording section, the recording may be performed at the time of product shipment, a distributed recording medium may be used, or download may be performed through the internet.

Further, for the respective steps in the flowcharts, the execution order may be altered, a plurality of steps may be concurrently executed, or the steps may be in an order that is different for each execution, as long as there is no inconsistency with the characteristics.

Note that parts described as "section" in the embodiments may be configured by combinations of dedicated circuits or a plurality of general-purpose circuits, and may he configured by combinations of processors such as a microcomputer configured to operate in accordance with previously programmed software, and a CPU, or sequencers such as an FPGA, as necessary.

The present invention is not limited only to the above respective embodiments, and can be embodied while component elements are modified without departing from the gist, in the implementation phase. Further, various inventions can be formed by appropriate combinations of a plurality of component elements disclosed in the above respective embodiments. For example, some component elements of all component elements shown in the embodiments may he excluded. Furthermore, component elements across different embodiments may be appropriately combined.

What is claimed is:

1. A wireless endoscope comprising:
   a wireless receiving circuit configured to receive a wirelessly transmitted voice;
   a first processor configured to process the voice;
   a light source configured to generate illumination light;
   an image pickup sensor configured to pick up an image of the subject; and
   a second processor configured to control the light source based on a processing result of the first processor.

2. A wireless endoscope apparatus comprising a wireless endoscope and a voice detection unit,
   the voice detection unit including:
      a microphone configured to acquire a voice;
      a voice modulation circuit configured to modulate the voice; and
      a first wireless transmission circuit configured to wirelessly transmit a modulation result of the voice modulation circuit,
   the wireless endoscope including:
      a wireless receiving circuit configured to receive the modulated voice;
      a first processor configured to process the modulated voice received by the wireless receiving circuit;
      a light source configured to generate illumination light;
      an image pickup sensor configured to pick up an image of the subject;

a second wireless transmission circuit configured to wirelessly transmit an image pickup result of the image pickup sensor; and a second processor configured to control the light source based on a processing result of the first processor; and wherein the voice detection unit is removably provided on the wireless endoscope.

3. The wireless endoscope apparatus according to claim 2, wherein the second processor is configured to control light emission of the light source based on the processing result.

4. The wireless endoscope apparatus according to claim 2, wherein the voice detection unit includes a battery.

5. The wireless endoscope apparatus according to claim 1, wherein the second processor is configured to put the first processor into an operating state, when the second processor detects that the voice detection unit is mounted on the wireless endoscope, based on a receiving result of the wireless receiving circuit.

6. The wireless endoscope apparatus according to claim 1, wherein the second processor is configured to put the first processor into a non-operating state, when the second processor detects that the voice detection unit is detached from the wireless endoscope, based on a receiving result of the wireless receiving circuit.

7. The wireless endoscope apparatus according to claim 2, wherein the wireless endoscope includes a power transmission circuit, and the voice detection unit includes a power receiving circuit configured to receive electric power from the power transmission circuit.

8. The wireless endoscope apparatus according to claim 7, wherein the voice detection unit is removably provided on the wireless endoscope.

9. The wireless endoscope apparatus according to claim 8, wherein the second processor is configured to put the first processor into an operating state, when the second processor detects that the voice detection unit is mounted on the wireless endoscope, based on a power transmission result of the power transmission circuit.

10. The wireless endoscope apparatus according to claim 8, wherein the second processor is configured to put the first processor into a non-operating state, when the second processor detects that the voice detection unit is detached from the wireless endoscope, based on a power transmission result of the power transmission circuit.

11. The wireless endoscope apparatus according to claim 8, wherein the second processor is changed to an operating state, when the voice detection by the voice detection unit detects that the voice detection unit is mounted on the wireless endoscope, based on a power transmission result of the power transmission circuit.

12. The wireless endoscope apparatus according to claim 8, wherein the second processor is changed to a non-operating state, when the second processor detects that the voice detection unit is detached from the wireless endoscope, based on a power transmission result of the power transmission circuit.

13. An illumination control method comprising:
acquiring a voice of a subject through a microphone sensor,
picking up an image of vocal cords of the voice acquired through the microphone sensor,
evaluating a voice frequency from the voice,
generating a light emission control signal based on the voice frequency; and
controlling an emission frequency of a light source based on the light emission control signal.

14. The illumination control method according to claim 13, further comprising observing the image of the vocal cords;
wherein the light source illuminates the vocal cords under observation.

15. The illumination control method according to claim 13, wherein the acquiring comprises wirelessly receiving the voice frequency from the microphone sensor.

16. The wireless endoscope according to claim 1, wherein the first processor is configured to evaluate a voice frequency of the voice, wherein the image pickup sensor is configured to pick up an image of vocal cords of the voice.

17. The wireless endoscope according to claim 16, further comprising a wireless transmission circuit configured to wirelessly transmit an image pickup result of the image pick up sensor.

18. The wireless endoscope according to claim 16, wherein the second processor is configured to generate a light emission control signal based on the voice frequency, the second processor is configured to control the light source based on the light emission control signal.

19. The wireless endoscope according to claim 16, wherein the second processor is configured to generate a light emission control signal based on a light emission frequency different from the voice frequency, the second processor is configured to control the light source based on the light emission control signal.

* * * * *